US010238343B2

(12) United States Patent
Goossen et al.

(10) Patent No.: US 10,238,343 B2
(45) Date of Patent: Mar. 26, 2019

(54) OPTICALLY ADAPTABLE BREAST COMPRESSION ELEMENT (71) Applicant: KONINKLIJKE PHILIPS N.V., Eindhoven (NL)

(72) Inventors: Andre Goossen, Radbruch (DE); Kars-Michiel Hubert Lenssen, Veldhoven (NL); Thomas Pralow, Buchholz i.d.N. (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 696 days.

(21) Appl. No.: 14/407,977

(22) PCT Filed: May 29, 2013

(86) PCT No.: PCT/IB2013/054445
§ 371 (c)(1),
(2) Date: Dec. 15, 2014

(87) PCT Pub. No.: WO2014/001925
PCT Pub. Date: Jan. 3, 2014

(65) Prior Publication Data
US 2015/0164426 A1 Jun. 18, 2015

Related U.S. Application Data (60) Provisional application No. 61/663,642, filed on Jun. 25, 2012.

(51) Int. Cl.
A61B 5/00 (2006.01)
A61B 6/04 (2006.01)
A61B 6/00 (2006.01)
A61B 8/08 (2006.01)
A61B 5/055 (2006.01)
(Continued)

(52) U.S. Cl.
CPC ............ A61B 5/708 (2013.01); A61B 5/0555 (2013.01); A61B 5/6843 (2013.01); A61B 5/743 (2013.01);
(Continued)

(58) Field of Classification Search
CPC ....... A61B 5/103; A61B 5/1077; A61B 5/708; A61B 5/0555; A61B 5/7445; A61B 5/743; A61B 8/0825; A61B 8/403
See application file for complete search history.

(56) References Cited

U.S. PATENT DOCUMENTS 5,541,972 A  7/1996  Anthony
6,682,484 B1  1/2004  Entrekin et al.
(Continued)

OTHER PUBLICATIONS

Lenssen et al: Bright e-Skin Technology and Applications: Simplified Gray-Scale E-Paper; Journal of the SID, Jan. 19, 2011, pp. 1-7.
(Continued)

Primary Examiner — Joseph M Santos Rodriguez
(74) Attorney, Agent, or Firm — Larry Liberchuk (57) ABSTRACT The present invention relates to compression of breasts during mammography, and in particular to a compression element for a breast holding arrangement for mammography examinations. In order to ensure an increased user comfort and an improved application of pressure force, a compression element (10) for a breast holding arrangement for mammography examinations is provided, comprising a supporting structure (12), a first surface (14), and a second surface (16). The supporting structure is configured to be attached to a mounting structure for exerting a compression force on a breast under examination. The first and second surfaces are attached to the support structure; and the first and second surfaces are arranged facing in opposite directions. The second surface is provided to compress the breast under examination. The first surface is provided to be visible
(Continued)

to a user, wherein the first surface is provided as an optically adaptable surface (18). The first and second surfaces are provided to be at least temporarily partly transparent.

16 Claims, 7 Drawing Sheets

(51) Int. Cl.
*A61B 6/03* (2006.01)
*A61B 8/00* (2006.01)

(52) U.S. Cl.
CPC ............ *A61B 5/7445* (2013.01); *A61B 6/037* (2013.01); *A61B 6/0414* (2013.01); *A61B 6/461* (2013.01); *A61B 6/502* (2013.01); *A61B 8/0825* (2013.01); *A61B 8/403* (2013.01)

(56) References Cited

U.S. PATENT DOCUMENTS

| | | |
|---|---|---|
| 7,505,555 B2 | 3/2009 | Hermann et al. |
| 7,792,244 B2 | 9/2010 | DeFreitas et al. |
| 2004/0267165 A1* | 12/2004 | Sarvazyan ............ A61B 5/0002 600/587 |
| 2005/0036584 A1 | 2/2005 | Lebovic et al. |
| 2008/0087830 A1 | 4/2008 | Kashiwagi |
| 2009/0213986 A1 | 8/2009 | Thaler |
| 2009/0290679 A1* | 11/2009 | Mikami ................ A61B 6/0414 378/37 |
| 2010/0004539 A1* | 1/2010 | Chen .................... A61B 8/0825 600/445 |
| 2011/0273906 A1* | 11/2011 | Nichol ................. G02B 6/0076 362/607 |
| 2012/0020464 A1 | 1/2012 | Matsuura |
| 2012/0050838 A1* | 3/2012 | Hirano ................... G02F 1/155 359/273 |
| 2012/0150034 A1 | 6/2012 | DeFreitas et al. |

OTHER PUBLICATIONS

Lenssen et al: "Novel Concept for Full-Color Electronic Paper"; Journal of the SID Apr. 17, 2009, pp. 383-388.

* cited by examiner

OPTICALLY ADAPTABLE BREAST COMPRESSION ELEMENT

CROSS-REFERENCE TO PRIOR APPLICATIONS

This application is the U.S. National Phase application under 35 U.S.C. § 371 of International Application No. PCT/IB2013/054445, filed on May 29, 2013, which claims the benefit of U.S. Provisional Patent Application No. 61/663642, filed on Jun. 25, 2012. These applications are hereby incorporated by reference in their entirety herein.

FIELD OF THE INVENTION

The present invention relates to compression of breasts during mammography, and relates in particular to a compression element for a breast holding arrangement for mammography examinations, to a mammography imaging system and to a method for mammography examinations, as well as to a computer program element and to a computer readable medium.

BACKGROUND OF THE INVENTION

For mammography examinations, compression paddles, or compression elements, are used to transfer a compression force onto a breast. For example, the paddles may be flat or curved. In order to allow an evaluation of the positioning and compression, the compression paddles are transparent. Thus, the technician can visually control the applied compression. However, it has been shown that the application of the correct pressure is not only relevant for the reduction or minimization of pain on side of the examined person, but also for a proper image quality. U.S. Pat. No. 6,682,484 B1 describes a breast imaging system including compression plates for retaining a breast during examination. One of the compression plates is formed by a polymeric membrane, which is stretched under tension to provide a rigid but compliant retention surface.

SUMMARY OF THE INVENTION

There may be a need to provide a compression element ensuring an increased user comfort and an improved application of pressure force.

The object of the present invention is solved by the subject-matter of the independent claims, wherein further embodiments are incorporated in the dependent claims.

It should be noted that the following described aspects of the invention apply also for the compression element for a breast holding arrangement for mammography examinations, for the mammography imaging system, for the method for mammography examinations, for the computer program element and for the computer readable medium.

According to a first aspect of the present invention, a compression element for a breast holding arrangement for mammography examinations is provided, comprising a supporting structure, a first surface, and a second surface. The supporting structure is attachable to a mounting structure, i.e. the structure is configured to be attached to a mounting structure for exerting a compression force on a breast under examination. The first and second surfaces are attached to the support structure. The first and second surfaces are arranged facing in opposite directions. The second surface is provided to compress the breast under examination. The first surface is provided to be visible to a user. Further, the first surface is provided as an optically adaptable surface. The first and second surfaces are provided to be at least temporarily partly transparent.

The "compression element" is also referred to as compression paddle or compression panel. The temporal grade of transparency is provided to allow a view of the breast for aiding in positioning, for example. Instead of the transparency, the position of the breast, i.e. contacting surface and contour, as well as the overall contour of the breast, or the breast outline, can be detected with other means and displayed on the first surface.

The term "surface" refers to the layer providing the outer surface. The layer may have several sub-layers, i.e. it can be multilayered. The first and second surface can be provided as two separate panels or may be integrated on two opposite sides of a common panel. The second surface may be provided with a curved profile or being adaptable to a breast contour, for example as a flexible paddle. A transparent cover may be provided on top of either surface. Optical adaptability may be provided on the first side, but also on the second side in case of a transparent first side.

According to an exemplary embodiment, the optically adaptable surface is provided with a controllable pixel matrix configured to provide textual and/or graphical data visualization.

The textual or graphical data may comprise pressure information, patient name and data, or instructions for the procedure.

For example, the graphical and textual information is presented also at least partly during a part of the second state, i.e. during the opaque state.

According to an exemplary embodiment, the pixels are provided in an imaging area of the compression element, and the pixels are provided as a passive-matrix with switching elements arranged outside the imaging area.

The passive-matrix is free of switching elements like transistors. The "imaging area" refers to the area that is used for image acquisition purposes, i.e. for example the area where electromagnetic or sound waves pass the compression element for image acquisition.

For example, the imaging area refers to an area where X-ray radiations are passing the compression element in direction of a detector in order to generate X-ray image data.

For example, the imaging area refers to an area where ultrasound waves are passing the compression element in direction of a detector in order to generate ultrasound data.

According to an exemplary embodiment, in a first state, the compression element is provided with a first grade of light transmission, in which the compression element is at least partly transparent such that a patient's compressed breast is visible to a user and/or the patient, and in a second state, the compression element is provided with a second grade of light transmission, in which the light transmission is reduced such that the breast is invisible to a user and/or the patient.

According to an example, different grades of light transmission are provided in order to regulate the visibility of the breast of the patient.

According to an example, in a first state, the compression element is at least partly transparent, and in a second state, the compression element is non-transparent.

The second surface may be at least partly transparent. Further, in a first state, the first surface is at least partly transparent, and in a second state this first surface is non-transparent. In another example, the first surface is at least partly transparent and the second surface is configured to achieve first and second state of at least partly transparency and non-transparency.

According to an exemplary embodiment, the first surface is provided as an adaptable display surface for providing positioning and/or compression information to the user.

According to an exemplary embodiment, the first surface is configured to provide graphical positioning information in accordance with a determined mammography examination, wherein the mammography examination comprises i) X-ray mammography image acquisition, ii) ultrasound mammography image acquisition, iii) positron emission mammography imaging, and/or iv) magnetic resonance mammography imaging.

In addition, or alternatively, the mammography examination can comprise magnetic resonance tomography or tomosynthesis.

According to an exemplary embodiment, the first surface is provided as a layer comprising electronic ink, wherein the change of the optical appearance is based on in-plane electrophoresis.

For example, the first surface may be provided in Philips e-skin technology.

According to an exemplary embodiment, the first surface is provided with an adaptable display layer with a plurality of first sub-areas arranged in a distance to each other. The first surface is also provided with a switchable layer to regulate a grade of transparency of second sub-areas provided between the first sub-areas.

For example, the first sub-areas are provided with an e-paper technology, wherein the optical appearance can be adjusted to different colours or grey-scale values. The first sub-areas are provided with an e-skin technology, in another example, wherein the optical appearance can be adjusted to different colours or grey-scale values and a grade of transparency can be adjusted.

The switchable surface may be provided as an electro-kinetic layer or as an electro-chromic layer. Instead of the e-paper technology, an LCD can be provided.

According to an exemplary embodiment, the first surface is provided as an interactive surface for control of mammography examinations.

For example, the compression element provides the possibility for control of an examination apparatus for the mammography examination. In one example, the first surface is provided as a touch sensitive surface or touch screen, at least for some areas or as a complete touch sensitive surface.

According to an exemplary embodiment, the second surface is provided with pressure-sensitive sensors for measuring touch and/or pressure acting on the breast to be examined. The pressure sensitive sensors are provided as a resistive or capacitive touch-sensing layer, or a pressure sensitive layer with electronic ink, to which ink an alternate current (AC) field is applied.

According to an exemplary embodiment, a first layer with electronic ink is provided as the optically adaptable surface, and a second layer with electronic ink is provided as the pressure sensitive layer.

According to a second aspect of the present invention, a mammography imaging system is provided, comprising an imaging device, a processing unit, and a breast holding arrangement. The imaging device is configured to acquire image data of a breast to be examined. The breast holding arrangement comprises a support element supporting the breast during the imaging procedure, and a compression element for applying a compression force during the imaging procedure. The compression element is provided as a compression element according to one of the above-mentioned examples.

According to an exemplary embodiment, the breast holding arrangement is provided with measurement sensors for measuring a compression force F applied to the breast between the support element and the compression element.

According to a third aspect of the present invention, a method for mammography examinations is provided, comprising the following steps:
a) arranging a breast to be examined between a support element and a compression element and compressing the breast; wherein during the arranging, the compression element is provided in a first at least partly transparent state;
b) adapting an optically adaptable first surface, which is provided to be visible to a user, such that the visible appearance is changed; for example, the compression element is transferred into a non-transparent second state;
c) conducting a determined examination of the breast; wherein the examination comprises acquiring at least one image of the breast.

In an example of the method, the compression applied to the breast is measured and compression information is provided on the optically adaptable surface at least during steps a) and b).

According to an aspect of the present invention, the compression element is provided as an interactive breast compression element, for example by using an e-paper/e-skin display that can be used to guide positioning, reproduce diagnostic quality for contra lateral views and may show diagnostic information, such as dense areas, location of suspicions marked by the radiologist, etc. Furthermore, such an interactive breast compression element can also be used to blind the patients view onto the breast during biopsy or image acquisition. Thus, the user's feeling of comfort is increased. Especially for biopsies, a non-transparent compression element is helpful for conducting the biopsy itself. However, for positioning, it is at least partly transparent to allow a better view to the breast. A visual positioning and compression aid on the panel improves the positioning. The displayed information and positioning information can be individualized for the respective examination. Thus, instead of being static information, the adaptable paddle also helps in preventing that important spots are covered by the instructions displayed thereon. An e-paper, such as Philips e-skin technology, is transparent to X-ray radiation and therefore does not provide any further intensity modulations and also does not introduce additional patterns to the X-ray image. It can be switched between a highly optically transparent state and opaque states. In contrast to other displays, it is highly resistant to external forces and pressure. E-skin can also be bent and is thus also suited for curved compression elements. For example, in case of an acrylic glass vat used as compression element, the bottom layer can be replaced by an e-skin element. For example, the e-skin element can be a pixel matrix that controls any graphical type of information in several grey levels between fully transparent and fully opaque. Thus, it is possible to display, for example, a coarse visualization of a previous mammogram, a map of breast density levels for different regions, suspicious regions marked in a previous mammogram, or all of the above after a registration and deformation of the outline of the previous mammogram with the actual outline of the compressed breast. Furthermore, non-image-related visualization is possible, such as distribution of compression force/pressure throughout the breast, non-compressed tissue at the border but especially within the interior parts of the breast, contour upon image formation for comparison and movement detection, e.g. for biopsies, patient information and patient distraction (the patient seeing something happens), or any combination of the above. Providing an e-skin pixelated display with a passive-matrix backplane, meaning that no switching elements like transistors are needed within the X-ray imaging area, a damage by X-ray radiation on the long term run is prevented. Further, the e-skin technology could be at least partially consisting of a segmented display, i.e. for parts of the paddle, only combinations of predetermined elements can be switched to transparent or dark state. The attenuation filter material in the tube may be adapted to the attenuation properties of the e-skin material, for example, thus insuring the spectrum passing through the patient's breast is still optimal for breast imaging. According to an aspect, means to identify or measure touch or pressure either globally or spatially distributed are provided. For example, both information visualization and pressure sensing are done using the same e-skin layer but with direct current (DC) respectively alternating current (AC) driving signals. As the absorption and modulation of e-skin within the part of X-ray is very small, the element does not have to be exchanged, but can be used for any examination. Another advantage is that the e-skin can be arranged on or integrated in the paddle provided in front of the breast tissue (viewed in direction of the X-ray radiation), such that once the breast has been radiated, no medically relevant intensity modulations are changed by absorption of the paddle with an e-skin layer. Thus, instead of assessing the breast compression via the force applied to the arm pressing down the paddle, the correct amount of breast compression for a specific patient's breast can be determined. For example, the current pressure and the breast outline can be used to predict a target outline with assumed optimum pressure and this can be visualized on the compression element. Thus, the technician would not have to deal with the force or pressure as an indirect physical property anymore, but could perform compression directly matching the actual and optimum contour of the breast. Further, in another embodiment, the touch sensor could identify skin folds, e.g. areas where the skin overlaps and as the result produces dips within the breast height. This would avoid two consequences: i) skin folding is especially painful under high pressure, ii) diagnostic image quality, but especially quantitative or physical measurements related from the mammogram, e.g. breast density assessment, suffering from skin folds. According to an aspect, it is possible to provide the information visualization and the pressure sensing using the same e-skin layer. An integrated touch sensing is of particular interest because no additional components are needed which could attenuate or modulate the X-ray.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
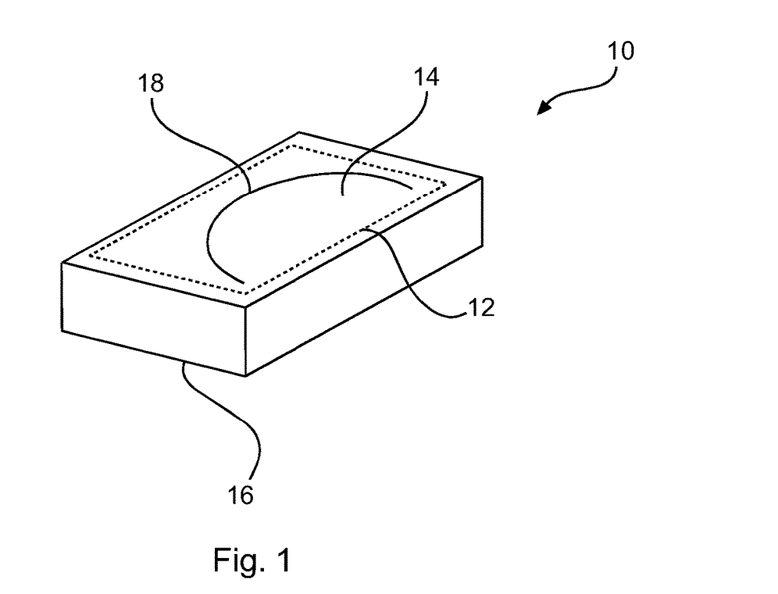
FIG. 1 shows an exemplary embodiment of a compression element in a schematic illustration in perspective view.

FIG. 1 shows a perspective view of a compression element 10 for a breast holding arrangement for mammography examinations. The compression element 10 comprises a supporting structure 12, indicated with dotted lines only, and a first surface 14 and a second surface 16. The supporting structure is configured to be attached to a mounting structure for exerting a compression force on a breast under examination. The first and second surfaces 14, 16 are attached to the supporting structure 12. The first and second surfaces 14, 16 are arranged facing in opposite directions, for example in the FIG. 1 showing the first surface facing upwards and the second surface facing downwards. The second surface 16 is provided to compress the breast under examination. The first surface 14 is provided to be visible to a user. At least one of the first surface 14 and the second surface 16 is provided as an optically adaptable surface 18, and the first and second surfaces are provided to be at least temporarily partly transparent.

In one example, the first surface 14 is provided as the optically adaptable surface 18 and the second surface 16 is at least partly transparent. In another example, the second surface 16 is provided as the optically adaptable surface 18 and the first surface 14 is at least partly transparent.

Figure 2:
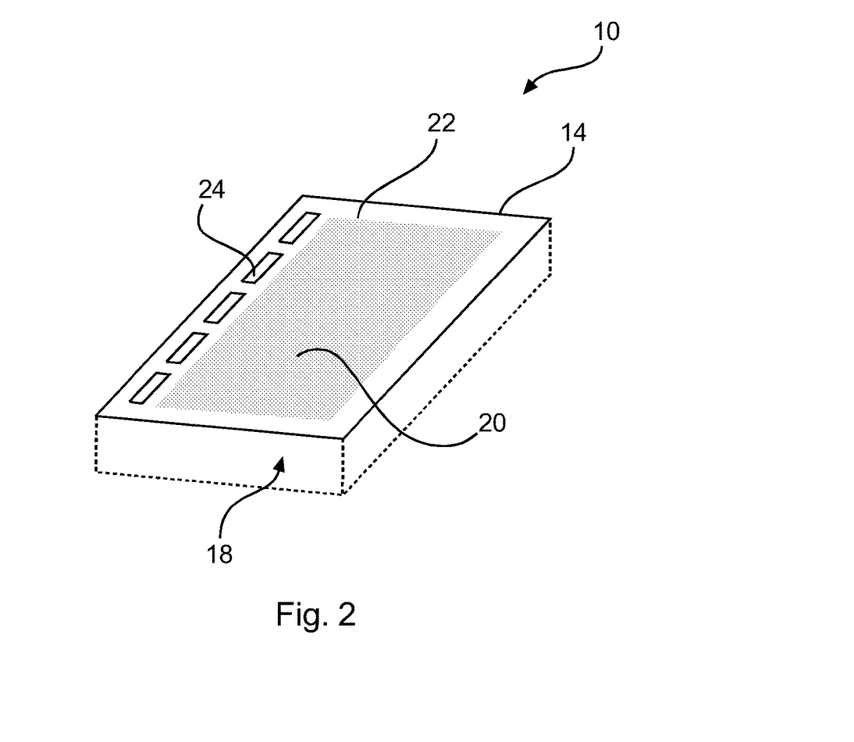
FIG. 2 shows a further embodiment of a compression element.

For example, as shown in FIG. 2, the optically adaptable surface 18 is provided with a controllable pixel matrix 20 configured to provide textual and/or graphical data visualization, not further shown.

According to a further example, also shown in relation with the above-mentioned features, but not meaning a necessary component of the above described example, the pixels are provided in an imaging area 22 of the compression element 10, wherein the pixels are provided as a passive-matrix with switching elements 24, i.e. transistor elements or circuit components, arranged outside the imaging area 22. The switching elements are provided for controlling the pixels of the pixel array. Although the switching elements are shown, they are hidden behind a housing or other structure and are thus not visible to a user. It is further noted that the switching elements are indicated schematically only; in reality they are much smaller than shown in FIG. 2.

For example, in a first state the compression element is at least partly transparent, and in a second state, the compression element is non-transparent. This can be seen, for example, in FIGS. 3 and 4, where in FIG. 3 the compression element shows graphical and textual information 26, whereas in FIG. 4, the compression element 10 is opaque.

Figure 3:
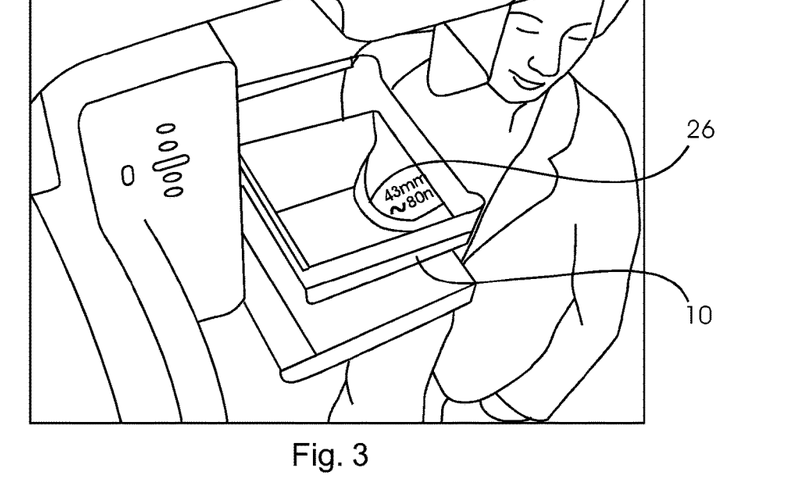
FIGS. 3 and 4 show perspective views of a compression element in relation with a mammography imaging system during an examination of a patient.
Figure 4:
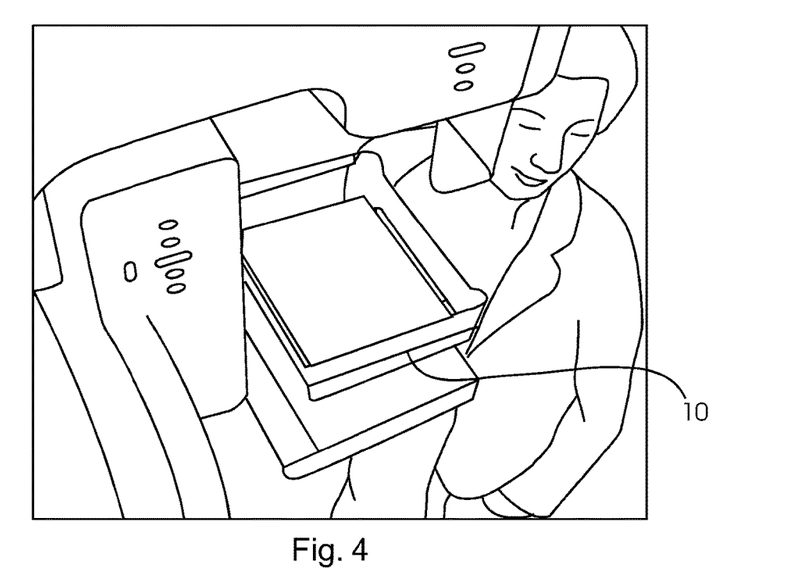

Instead of the non-transparency, the compression element can have a reduced transparency in which the breast is hardly visible. The lower light transmission may be provided with respect to a certain part of the optical spectrum, for example, to the range of visible light wavelengths.

In a further example (not shown), the graphical and textual information 26 is presented also at least partly during a part of the second state.

Thus, the first surface 14 is provided as an adaptable display surface for providing positioning and/or compression information to the user as shown in FIG. 3. For example, the textual and/or graphical data visualization is provided in the transparent or partly transparent state and in the non-transparent state, too. In the non-transparent state, the patient's view onto the breast is blinded. For example, the first surface non-transparent in the second state, as indicated above.

The term "non-transparent" refers to an opaque state, i.e. a state with no light transmission. The term also refers to a state with no direct light transmission, but with indirect light transmission such that light is transmitted in a diffuse manner, which is also referred to as translucent.

According to an alternative, the first surface is at least partly transparent. In a first state, the second surface is at least partly transparent, and in a second state, the second surface is non-transparent.

The information may comprise positioning and compression aid. The information is provided in a graphical manner, e.g. text or graphic instructions, such as outlines of a breast, contacting surfaces of a breast and the like. The optically adaptable surface is configured to show, e.g., a coarse visualization of a previous examination, as mentioned above. The optically adaptable surface is configured to show patient information in a further example. The optically adaptable surface may also be configured to show distraction to the user.

The first surface may be configured to provide graphical positioning information, as the one shown in FIG. 3, indicated with reference numeral 26, in accordance with a determined mammography examination, that may comprise an X-ray mammography image acquisition, ultrasound mammography image acquisition, positron emission mammography imaging, and/or magnetic resonance mammography imaging.

Figure 5:
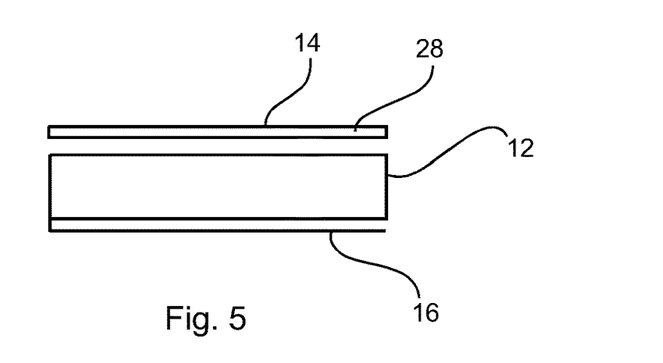
FIG. 5 shows a schematic cross section of a compression element in a further exemplary embodiment.

FIG. 5 shows a schematic cross-section of an example, where the first surface 14 is provided with a layer comprising electronic ink 28, wherein the change of the optical appearance is based on in-plane electrophoresis.

The electronic ink is driven, although not further shown, i.e. controlled by applying an external DC electric field.

The first surface may be provided as a bi-stable display, wherein the power supply is required only for the change of the display content. The display content is maintained without applying electric power.

The first surface may be provided as a layer with electronic ink, wherein the change of the optical appearance is based on electro-wetting.

For providing electric energy, photovoltaic cells or battery power supply can be integrated in the compression element.

For providing electric energy, a wireless power supply via inductive coupling with a mounting structure may be provided.

Figure 6:
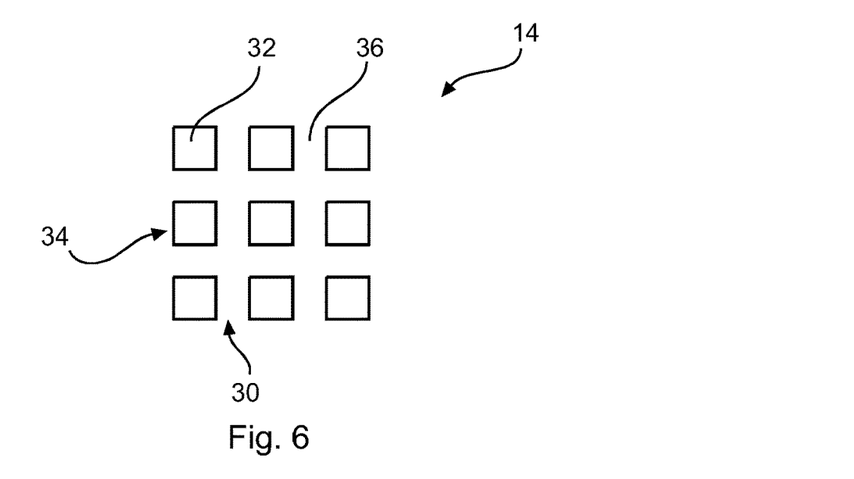
FIG. 6 shows a section of a plan view of a compression element in an exemplary embodiment.

According to a further example, indicated in FIG. 6, the first surface 14 is provided with an adaptable display layer 30 with a plurality of first sub-areas 32 arranged in a distance to each other. The first surface is also provided with a switchable layer 34 to regulate a grade of transparency of second sub-areas 36, provided between the first sub-areas 32.

Figure 7:
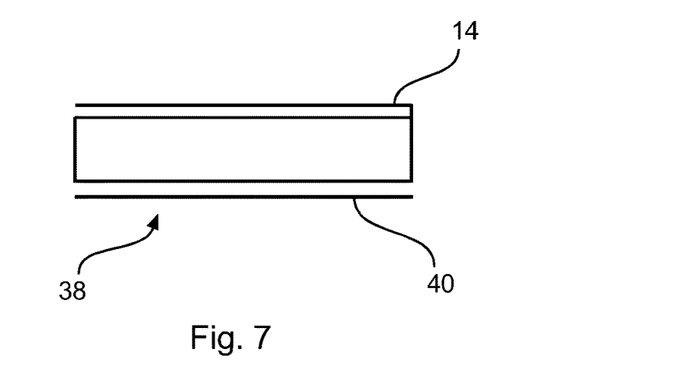
FIGS. 7 to 9 show further cross sections through exemplary embodiments of a compression element.

According to a further example, the second surface 16 is provided with pressure sensitive sensors 38 for measuring touch and/or pressure acting on the breast to be examined. For example, the pressure sensitive sensors 38 are provided as a resistive or capacitive touch sensing layer 40, as shown in FIG. 7.

In another example, for at least partly transparent pressure sensing, transparent carbon-nanotube based pressure sensors are provided. For example, a stretchable capacitor with transparent electrode is provided. Under pressure, for example when stretched or pressed, the distance of the capacitor layers is changed, and a pressure can be determined based on a change in capacitance.

According to a further example (not shown in detail), the first surface is provided as an interactive surface for control of mammography examinations. For example, the surface is provided at least with some touch sensitive areas which are provided for entering commands in relation with a mammography examination. For example, a pressure force can be manually adapted or set. Further, the interactive surface can be provided for manual feedback or for entering a response to indicated issues or questions, e.g. while being guided through the preparation steps for the mammography scan. The interactive surface is provided to be activated by the staff member(s) operating the mammography system. Alternatively or in addition, the interactive surface is provided to be activated by the person currently examined.

Figure 8:
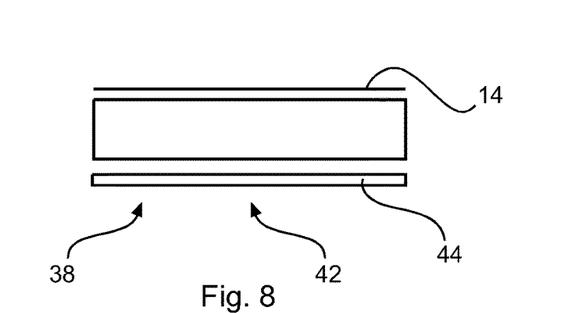

FIG. 8 shows a further example, wherein the pressure sensitive sensors 38 are provided as a pressure sensitive layer 42 with electronic ink 44, to which ink an AC field is applied.

The applied pressure is determined by a) measuring an area A where the breast touches the second surface; b) measuring a compression force F by the mounting structure that applies the compression force; c) computing an average pressure P via $P=F/A$; and as an option d) indicating to further compress or decompress via comparison with an optimum pressure, for example derived from empiric data.

Alternatively, the applied pressure can be directly estimated from the movement and count of e-ink particles within the observed areas of the pressure sensitive layer. In another embodiment, more than one layer of e-skin could be employed to directly measure the pressure onto the breast during compression and visualize it to the technician. By that, critical areas with high pressure can be identified soon, and the breast can be repositioned or the compression force can be adapted in order to maintain patient comfort. The current pressure and the breast outline can be used to predict a target outline with assumed optimum pressure. The target outline is presented on the optically adaptable surface. The pressure sensitive layer is configured to detect and identify skin folds, i.e. areas where the skin overlaps.

Figure 9:
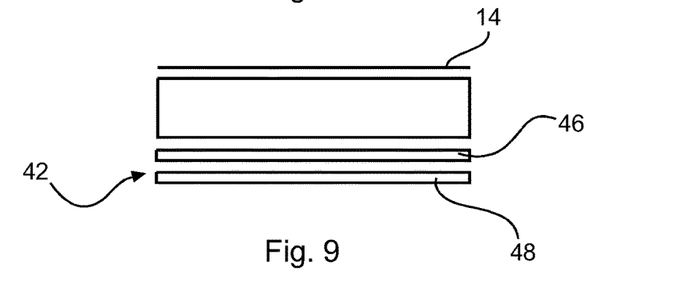

According to a further example, shown in FIG. 9, a first layer 46 with electronic ink is provided as the optically adaptable surface, and a second layer 48 is provided with electronic ink as the pressure sensitive layer 42. For example, both layers are provided on the lower side, i.e. on the side of the second surface 16. Thus, the upper side, i.e. the first surface 14 is only provided as a cover.

According to a further example, although not further shown, the arrangement is provided vice versa, i.e. the double electronic ink layers 46, 48 are provided on the first surface 14.

In another example, the pressure sensitive layer determines the applied pressure and the optically adaptable surface provides respective compression information and instructions to a user.

In another example, only one layer of electronic ink is provided with combining DC and AC current to provide different functions of the single electronic ink layer.

Figure 10:
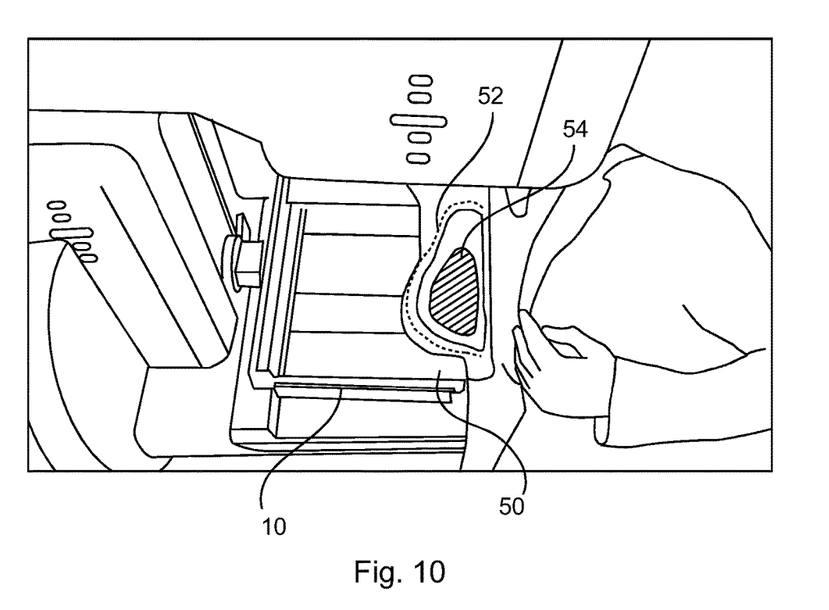
FIG. 10 shows a further exemplary embodiment of a compression element in relation with a mammography system during an examination of a patient.

FIG. 10 shows a further example of the compression element 10 during examination. Compression information is provided by the optically adaptable surface 18, for example indicating a pressure valve 50. Further, an outline 52 is indicated with a dashed line. Still further, an image, for example a previously acquired or only recently acquired X-ray image 54 is shown overlaid to the breast arranged underneath the compression plates.

Figure 11:
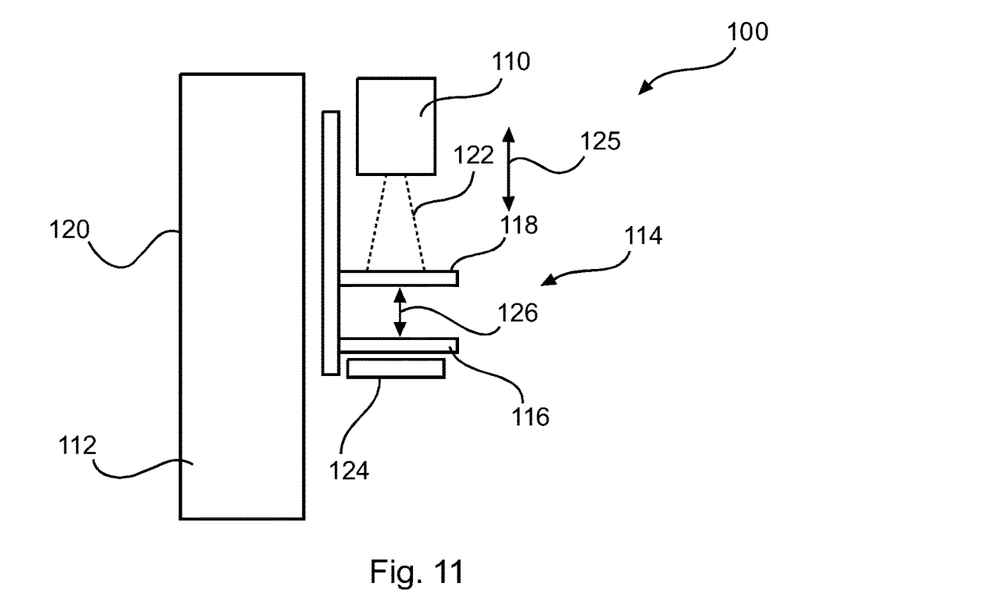
FIG. 11 shows a schematic setup of a mammography imaging system according to an exemplary embodiment.

FIG. 11 shows a mammography imaging system 100, comprising an imaging device 110, a processing unit 112, and a breast holding arrangement 114. The imaging device is configured to acquire image data of a breast to be examined. The breast holding arrangement 114 comprises a support element 116, supporting the breast during the imaging procedure, and a compression element 118 for applying a compression force during the imaging procedure. The compression element is provided as a compression element according to one of the above-mentioned examples. Further, a base structure is indicated in form of a housing structure 120. The imaging device 110 is an X-ray imaging system, radiating an X-ray beam, indicated with dotted lines 122. Further, a detector 124 is shown to be part of the imaging device 110.

A first double-arrow 125 indicates the height adaptability of the whole system, whereas a second double-arrow 126 indicates the movement possibility of the support element 116 in relation with the compression element 118.

According to a further example, the breast holding arrangement is provided with measurement sensors (not further shown) for measuring a compression force F applied to the breast between the support element 116 and the compression element 118.

Figure 12:
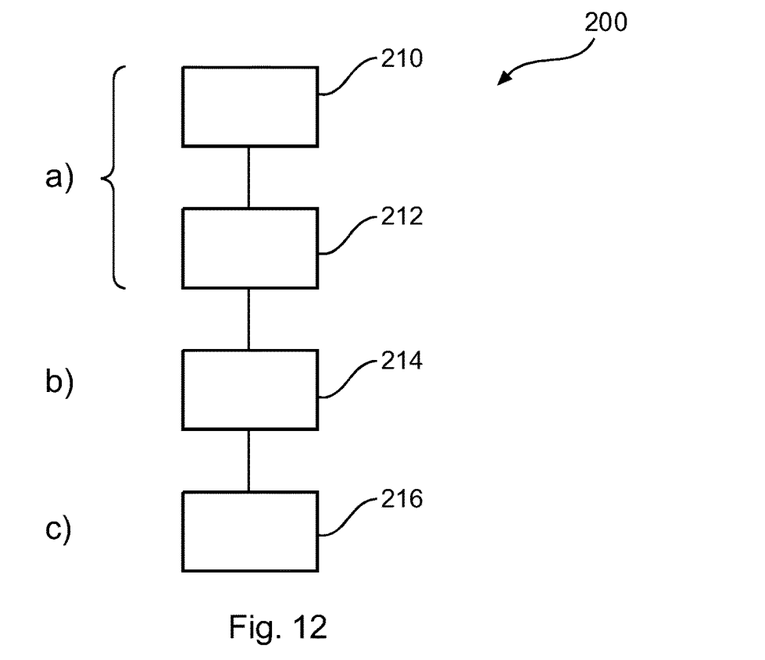
FIG. 12 shows basic steps of an exemplary method for mammography examinations.

Further, FIG. 12 shows a method 200 for mammography examinations, comprising the following steps: In a first sub-step 210, a breast to be examined is arranged between a support element and a compression element, and the breast is compressed in a second sub-step 212. The first and second sub-steps are referred to as a first step. In a second step 214, an optically adaptable first surface is adapted, which first surface is provided to be visible to a user, such that the visible adaptable surface is changed. For example, the compression element is changed into a non-transparent second state. In a third step 216, a determined examination of the breast is conducted, wherein the examination comprises acquiring at least one image of the breast.

The first step with the first sub-step 210 and the second sub-step 212 is also referred to as step a), the second step 214 as step b), and the third step 216 as step c).

Figure 13:
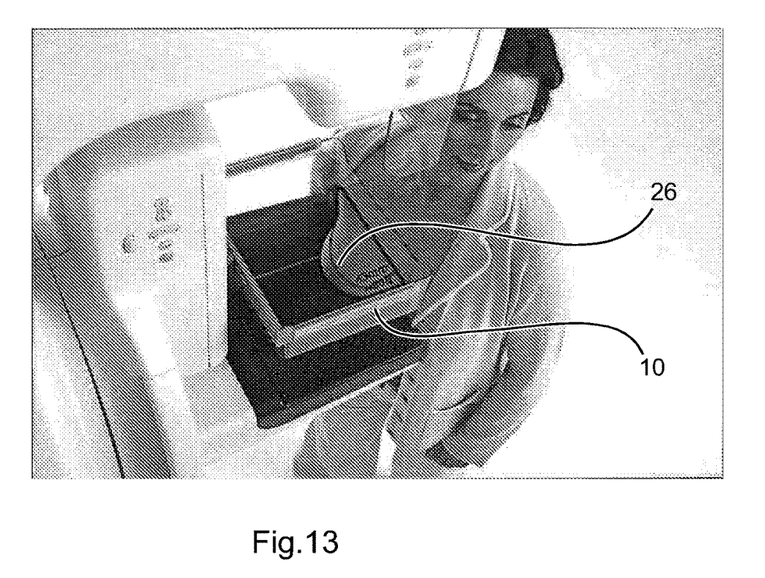
FIGS. 13 to 15 show photographic illustrations of the drawings of FIGS. 3, 4, and 10.
Figure 14:
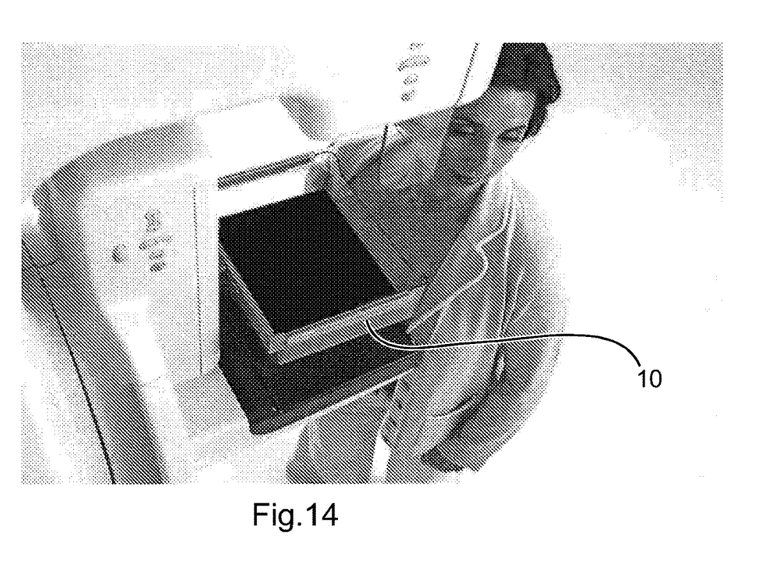
Figure 15:
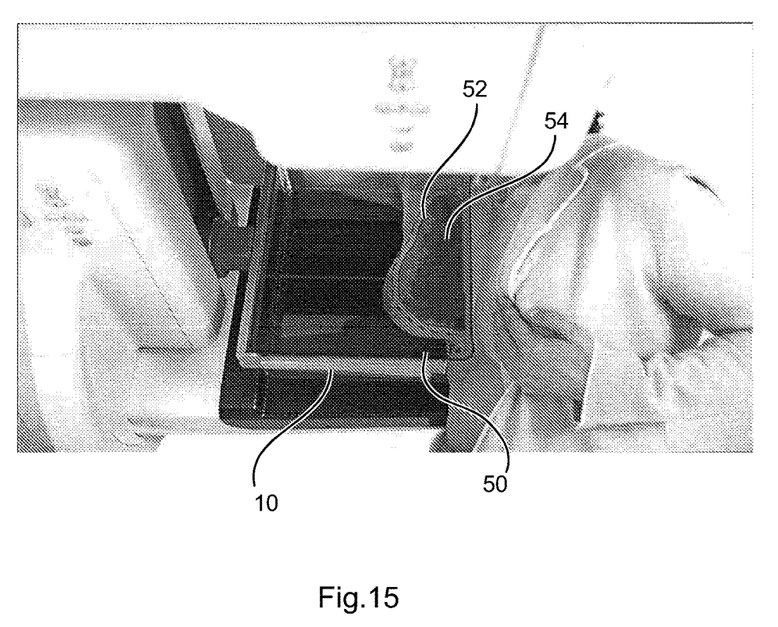

FIG. 13 shows a photographic illustration of the line drawing of FIG. 3, FIG. 14 shows a photographic illustration of FIG. 4, and FIG. 15 shows a photographic representation of FIG. 10.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A compression element for a breast holding arrangement for a mammography examination, the compression element comprising:
   a supporting structure configured to be attached to a mounting structure for exerting a compression force on a breast under examination;
   a first surface; and
   a second surface;
      wherein the first and second surfaces are attached to the supporting structure; wherein the first and second surfaces are arranged facing in opposite directions;
      wherein the second surface is provided to compress the breast under examination;
      wherein the first surface is provided to be visible to a user;
      wherein at least one of the first surface and the second surface is provided as an optically adaptable surface; and
      wherein at least one of the first and second surfaces is configured to change to different levels of transparency depending on a state of the mammography examination.

2. The compression element according to claim 1, wherein the optically adaptable surface is provided with a controllable pixel matrix configured to provide at least one of textual and graphical data visualization.

3. The compression element according to claim 2, wherein pixels of the controllable pixel matrix are provided in an imaging area of the compression element; and
   wherein the pixels are provided as a passive-matrix with switching elements arranged outside the imaging area.

4. The compression element according to claim 1, wherein in a first state, the at least one of the first and second surfaces is provided with a first level of transparency, in which the at least one of the first and second surfaces is at least partly transparent such that the breast is visible to at least one of a user and a patient, and in a second state, the at least one of the first and second surfaces is provided with a second level of transparency, in which light transmission is reduced such that the breast is not visible to the at least one of the user and the patient.

5. The compression element according to claim 1, wherein the first surface is configured to provide graphical positioning information in accordance with a determined mammography examination comprising at least one of:
   X-ray mammography image acquisition;
   ultrasound mammography image acquisition;
   positron emission mammography imaging; and
   magnetic resonance mammography imaging.

6. The compression element according to claim 1, wherein the first surface comprises a layer having electronic ink, wherein a change of optical appearance is based on in-plane electrophoresis.

7. The compression element according to claim 1,
   wherein the first surface is provided with an display layer with a plurality of first sub-areas arranged in a distance to each other; and
   wherein the first surface is also provided with a switchable layer to regulate a level of transparency of second sub-areas provided between the first sub-areas.

8. The compression element according to claim 1, wherein the first surface is provided as an interactive surface for at least one of controlling input and receiving feedback in mammography examinations.

9. The compression element according to claim 1,
   wherein the second surface is provided with pressure sensitive sensors for measuring at least one of touch and pressure acting on the breast to be examined; and
   wherein the pressure sensitive sensors are provided as:
      a resistive or capacitive touch sensing layer; or
      a pressure sensitive layer with electronic ink to which an Alternating Current (AC) field is applied.

10. The compression element according to claim 9, wherein a first layer with electronic ink is provided as the optically adaptable surface and a second layer with electronic ink is provided as the pressure sensitive layer.

11. A mammography imaging system, comprising:
   an image acquiring device configured to acquire image data of a breast to be examined; and
   a breast holding arrangement comprising a support element for supporting the breast during an imaging procedure, and a compression element for applying a compression force during the imaging procedure, the compression element comprising:
      a supporting structure configured to be attached to a mounting structure for exerting a compression force on a breast under examination;
      a first surface; and
      a second surface;
      wherein the first and second surfaces are attached to the supporting structure;
      wherein the first and second surfaces are arranged facing in opposite directions;
      wherein the second surface is provided to compress the breast under examination;
      wherein the first surface is provided to be visible to a user;
      wherein at least one of the first surface and the second surface is provided as an optically adaptable surface; and
      wherein at least one of the first and second surfaces is configured to change to different levels of transparency depending on a state of the mammography examination.

12. The mammography imaging system according to claim 11, wherein the breast holding arrangement is provided with measurement sensors for measuring a compression force applied to the breast between the support element and the compression element.

13. A method for a mammography examination, comprising:
   arranging a breast to be examined between a support element and a compression element and compressing the breast, wherein during the arranging, the compression element provides a first at least partly transparent state;
   adapting an optically adaptable at least one of a first surface and a second surface of the compression element visible to a user; and
   conducting the examination of the breast, wherein the examination comprises acquiring at least one image of the breast; and
   controlling the compression element wherein at least one of the first surface and the second surface change to different levels of transparency depending on a state of the mammography examination.

14. A non-transitory computer readable medium having stored a computer program which, when executed by a computer unit, is adapted to perform a method for a mammography examination, comprising:

compressing a breast arranged to be examined within a compression element, wherein during the arranging, controlling the compression element to provide a first at least partly transparent state;

adapting an optically adaptable at least one of a first surface and a second surface of the compression element visible to a user; and conducting a determined examination of the breast, wherein the examination comprises acquiring at least one image of the breast; and controlling the compression element wherein at least one of the first surface and the second surface change to different levels of transparency depending on a state of the examination.

15. The compression element according to claim 1, wherein the different levels of transparency include at least partly transparent and non-transparent.

16. The compression element according to claim 2, wherein the at least one of textual and graphical data visualization provide information to assist in determining positioning and compression of the breast.

\* \* \* \* \*